(12) United States Patent
Pagani et al.

(10) Patent No.: US 12,082,862 B2
(45) Date of Patent: Sep. 10, 2024

(54) SURGICAL SCREWDRIVER

(71) Applicant: MEDACTA INTERNATIONAL SA, Castel San Pietro (CH)

(72) Inventors: Luca Pagani, Castel San Pietro (CH); Marco Riva, Castel San Pietro (CH); Meinrad Fiechter, Castel San Pietro (CH); Francesco Siccardi, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 402 days.

(21) Appl. No.: 17/415,613

(22) PCT Filed: Dec. 17, 2019

(86) PCT No.: PCT/IB2019/060892
§ 371 (c)(1),
(2) Date: Jun. 17, 2021

(87) PCT Pub. No.: WO2020/128812
PCT Pub. Date: Jun. 25, 2020

(65) Prior Publication Data
US 2022/0054178 A1 Feb. 24, 2022

(30) Foreign Application Priority Data
Dec. 20, 2018 (IT) .......................... 102018000020290

(51) Int. Cl.
*A61B 17/88* (2006.01)
*B25B 13/48* (2006.01)
(Continued)

(52) U.S. Cl.
CPC ........ *A61B 17/8886* (2013.01); *B25B 13/481* (2013.01); *B25B 23/0014* (2013.01); *A61B 2017/00477* (2013.01)

(58) Field of Classification Search
CPC ............ A61B 17/8875; A61B 17/8877; A61B 17/888; A61B 17/8883; A61B 17/8886; A61B 17/8888; A61B 17/8891
See application file for complete search history.

(56) References Cited

U.S. PATENT DOCUMENTS 1,392,220 A    9/1921 Quint
5,797,918 A *  8/1998 McGuire ............ A61B 17/1714
                                                        606/104

(Continued)

FOREIGN PATENT DOCUMENTS

JP       58143165 U      9/1983
WO    2011008286 A1      1/2011

OTHER PUBLICATIONS

English Translation of Notice of Reasons of Refusal in JP 2021-535599, mailed Jul. 11, 2022, 9 pages.

(Continued)

*Primary Examiner* — Si Ming Ku
(74) *Attorney, Agent, or Firm* — Meunier Carlin & Curfman LLC

(57) ABSTRACT

Various implementations include a surgical screwdriver that comprises a first rotating shaft configured to be rotated about a respective longitudinal axis, a second rotating shaft extending along a respective development axis transverse to the longitudinal axis of the first shaft and having a shaped end tip which can be inserted into the head of a screw, and a transmission member interposed between respective first ends of the shafts to transfer the rotation from the first shaft to the second shaft. The transmission member comprises a homokinetic spherical joint.

7 Claims, 7 Drawing Sheets

(51) Int. Cl.
    *B25B 23/00*        (2006.01)
    *A61B 17/00*        (2006.01)

(56)           References Cited

U.S. PATENT DOCUMENTS

| | | |
|---|---|---|
| 6,347,564 B1 | 2/2002 | Ciocca |
| 7,082,864 B1 | 8/2006 | Weber |
| 2001/0021853 A1* | 9/2001 | Heckele ................ A61F 2/4611 606/104 |
| 2002/0007704 A1 | 1/2002 | Hahn |
| 2011/0197719 A1 | 8/2011 | Neitzell et al. |
| 2012/0109142 A1 | 5/2012 | Dayan |
| 2014/0018815 A1 | 1/2014 | Kirschman |
| 2014/0018816 A1 | 1/2014 | Fenn et al. |
| 2018/0325574 A1 | 11/2018 | Bjork et al. |
| 2022/0079646 A1 | 3/2022 | Pagani et al. |

OTHER PUBLICATIONS

International Search Report and Written Opinion, issued by the International Searching Authority (ISA/EP) in PCT Application No. PCT/IB2019/060892 on Apr. 1, 2020. 13 pages.

International Search Report and Written Opinion, issued by the International Searching Authority (ISA/EP) in PCT Application No. PCT/IB2019/060887 on Apr. 1, 2020. 13 pages.

Non-Final Office Action received in connection with U.S. Appl. No. 17/415,619, dated Aug. 24, 2023, 13 pages.

Notice of Allowance for U.S. Appl. No. 17/415,619 dated Apr. 4, 2024, 8 pages.

\* cited by examiner

SURGICAL SCREWDRIVER

TECHNICAL FIELD

The present invention relates to a surgical screwdriver, in particular one with a tilted axis, used to operate on screws or other threaded elements that attach to bone tissue.

PRIOR ART

Surgical screwdrivers are used to screw/unscrew clamping screws in various applications such as anterior interbody arthrodesis, where it is necessary to bind appropriate inserts to the vertebrae using the above-mentioned clamping screws.

In this specific case, the operator pierces the patient's skin by making an incision of just a few centimetres in order to insert the surgical tools, including the screwdriver.

In order to carry out an operation that is as minimally invasive as possible, therefore, the screwdrivers and other tools are kept coincident with the axis of the hole defined by the incision, i.e. with their development axis perpendicular to the surface on which the incision is made.

In this situation, in fact, the screwdriver must not be tilted in order to avoid widening the incision and, thus, tearing the skin tissue.

However, the clamping screws may have their own rotation axis, at the respective application site, that does not coincide with the axis of the hole defined by the incision.

In this situation, tilted-axis surgical screwdrivers are used and equipped with a longitudinal rod from which a shaped tip extends that is designed be inserted into the head of the screw and extending transversely to the rod.

In particular, the rod has a first end that is intended to remain outside the patient's body and on which the operator transmits the rotational motion.

On the opposite side of the first end, a second end of the rod extends and is rotatably engaged with the shaped tip.

Between the second end of the rod and the shaped tip, a joint, typically a cardan joint, extends, which is capable of transferring the rotational motion of the rod to the shaped tip.

In particular, the joint consists of a first fork extending from the second end of the rod and a second fork from which the shaped tip extends. The forks are mutually pivoted using a cross-shaped element that enables the connection of the forks and the possibility of staggering the tip with respect to the rod.

In this way, the joint allows the rod to be kept aligned with the incision hole and, at the same time, to operate by screwing/unscrewing the screw positioned along an axis that is tilted with respect to the longitudinal extension of the rod itself.

The surgical screwdrivers described above, although capable of transferring the rotational motion between two transverse axes (rod axis and shaped tip axis), have, in any case, significant drawbacks.

A first, significant drawback is the transmission ratio between the rod and the shaped tip. It is well known that in this type of transmission the instantaneous angular velocity of the shaped tip (driven shaft) is not constant during a complete rotation but is a function of the misalignment angle of the shaped tip (driven shaft) axis with respect to the shaft axis (drive shaft). As the angle of incidence increases, the amplitude of oscillation of the angular velocity also increases.

There is, therefore, a non-fluid transmission between the rod and the shaped tip, which can generate vibrations and, during the operation on the screw, misalign the shaped tip with respect to the screw head. In this context, it is particularly uncomfortable for the operator to operate precisely and efficiently on the clamping screws.

Another significant drawback of the prior art described above is the overall dimensions of the cardan joint. In this context, it is very difficult to insert the screwdriver through small incisions. The presence of the two forks connected to each other means, in fact, that the screwdriver is considerably enlarged in a direction transverse to the longitudinal extension of the rod. For this reason, in order to enable the complete insertion of the joint, the surgical operator cannot keep the incision very small.

Finally, a further drawback, which is again linked to the presence of the cardan joint, is the presence of projecting elements that, in certain applications, may inadvertently interfere with the tissues surrounding the clamping screw.

In this case, in fact, the two forks of the cardan joint cause transverse projections that, during rotation, may engage the soft tissues close to the operating site and damage them.

The purpose of the present invention is, therefore, to make a surgical screwdriver available that overcomes the drawbacks of the prior art described above.

A first purpose of the present invention, in fact, is to propose a surgical screwdriver with a tilted axis capable of transmitting, in an almost constant way, the angular velocity transmitted by the surgeon, therefore ensuring a stable and precise operation on the clamping screw.

An additional purpose of the present invention is to propose a surgical screwdriver of limited dimensions in cross-section, in order to make the surgical operation as non-invasive as possible.

Finally, one purpose of the present invention is to propose a surgical screwdriver with tilted axes and equipped with a compact transmission joint without any roughness or projections that could interfere with the soft tissues surrounding the operating site.

These and other purposes are substantially attained by a surgical screwdriver, in particular with a tilted axis according to what is described in one or more of the accompanying claims.

SUMMARY

In particular, according to a first aspect, the present invention concerns a surgical screwdriver comprising a first rotating shaft configured to be rotated about a respective longitudinal extension axis and a second rotating shaft extending along a respective development axis and having a shaped end tip to be inserted into the screw head. A transmission member, which is interposed between the respective first shaft ends to transfer the rotation from the first shaft to the second shaft, is provided.

The transmission member advantageously comprises a homokinetic spherical joint.

The spherical joint preferably comprises a spherical head having at least one lateral facet and a cavity counter-shaped to said head and partially surrounding the head itself.

The head preferably comprises a plurality of lateral facets adjacent to each other, each defining a respective segment of the spherical head. The head also comprises a plurality of edges, each of which is interposed between two adjacent facets.

The spherical head is preferably joined to the first end of one of the shafts and has, along a section plane coinciding with the axis of the respective shaft, a circular profile and, along a section plane perpendicular to the axis, a polygonal profile.

The spherical head is preferably joined to the first end of the first shaft and the cavity is located on the first end of the second shaft. The first end of the second shaft is advantageously arranged on the opposite side to the above-mentioned shaped tip.

An internally hollow cylindrical sleeve is preferably provided to accommodate the shafts and the homokinetic spherical joint. The first shaft has a second end opposite the first and projecting outside a first opening of the sleeve. The shaped tip of the second shaft projects, instead, outside a second opening of the sleeve, opposite the first opening.

In accordance with a first embodiment of the invention, the sleeve openings are preferably not coaxial with each other and the second opening defines the development axis of the second shaft transverse to the longitudinal axis of the first shaft.

The sleeve preferably comprises a projection defining a spherical outer surface for accommodating the homokinetic spherical joint.

The first shaft preferably comprises two portions coaxially joined to each other inside the sleeve; in this situation the second end of the first shaft is located in one of the portions distal to the second shaft.

The cylindrical sleeve preferably also comprises an ergonomic portion arranged on an outer surface of the sleeve near the second end of the first shaft. The shafts are rotatable inside the sleeve around their respective axes and with respect to the sleeve itself.

In accordance with a second embodiment of the invention, the first end of the first shaft preferably comprises a circular seat coaxial to the longitudinal axis of the first shaft itself. The spherical head has a coupling pin projecting from the head and accommodated in said circular seat.

In this situation, an internally hollow cylindrical body, which is coaxially engaged with the first end of the first shaft, is preferably provided. The homokinetic spherical joint is accommodated inside said cylindrical body.

The cylindrical body preferably comprises a through opening through which the shaped tip of the second shaft projects; the second shaft is mobile inside said opening to orient itself in a plurality of operating configurations, each of which is representative of a respective angle of incidence between the longitudinal axis of the first shaft and the development axis of the second shaft.

An elastic thrust member, which is interposed between the circular seat of the first shaft and the coupling pin, is preferably provided to allow the movement of the second shaft and the homokinetic spherical joint towards the first shaft.

Additional features and advantages will emerge in greater detail in the description of a preferred, but not exclusive, embodiment of a surgical screwdriver, according to the present invention and the dependent claims.

BRIEF DESCRIPTION OF THE DRAWINGS

The present invention will be made clearer by the following detailed description, with reference to the attached drawings provided by way of example only, wherein.

DETAILED DESCRIPTION

Figure 1:
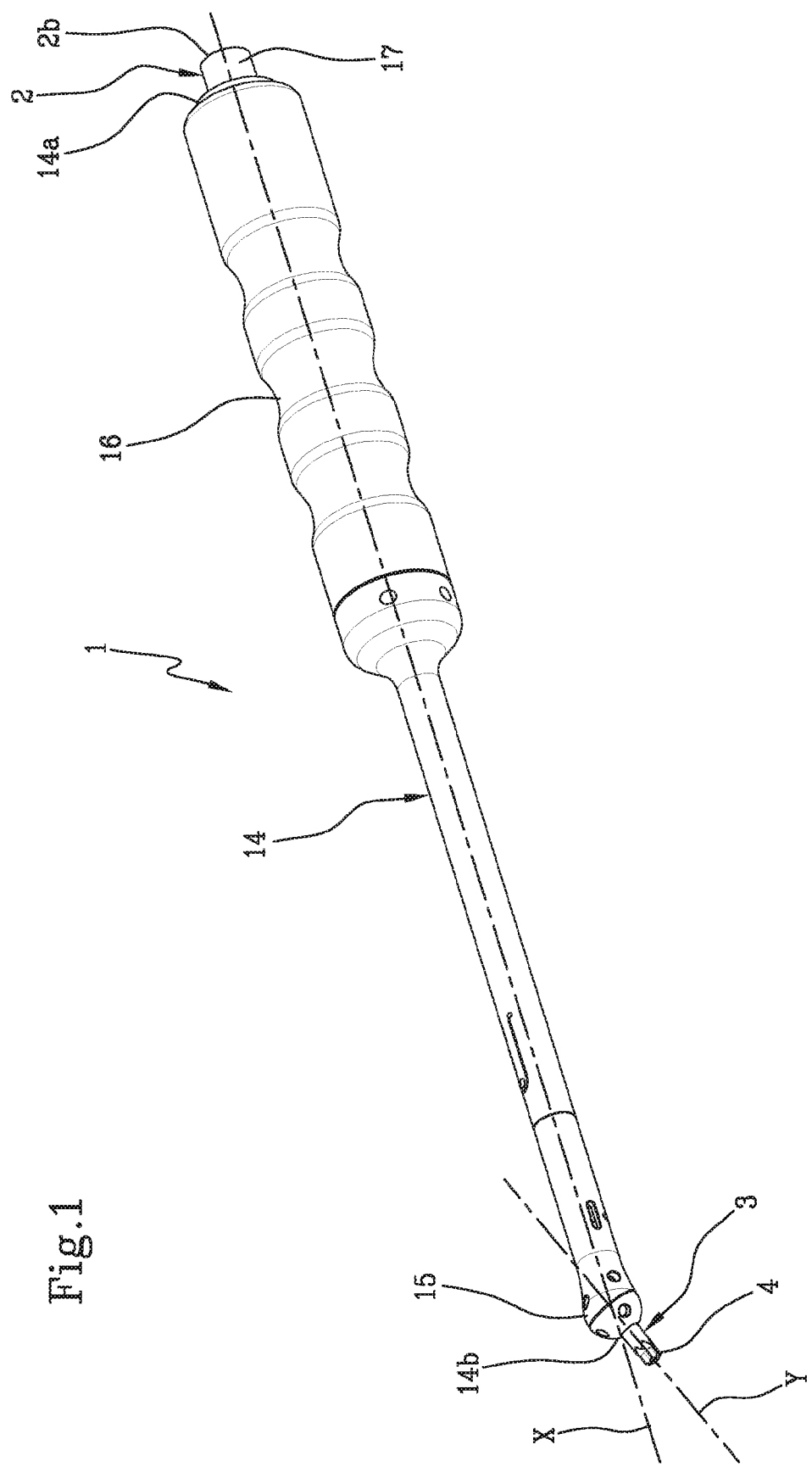
FIG. 1 shows a perspective view of a surgical screwdriver in accordance with a first embodiment of the present invention.
Figure 2:
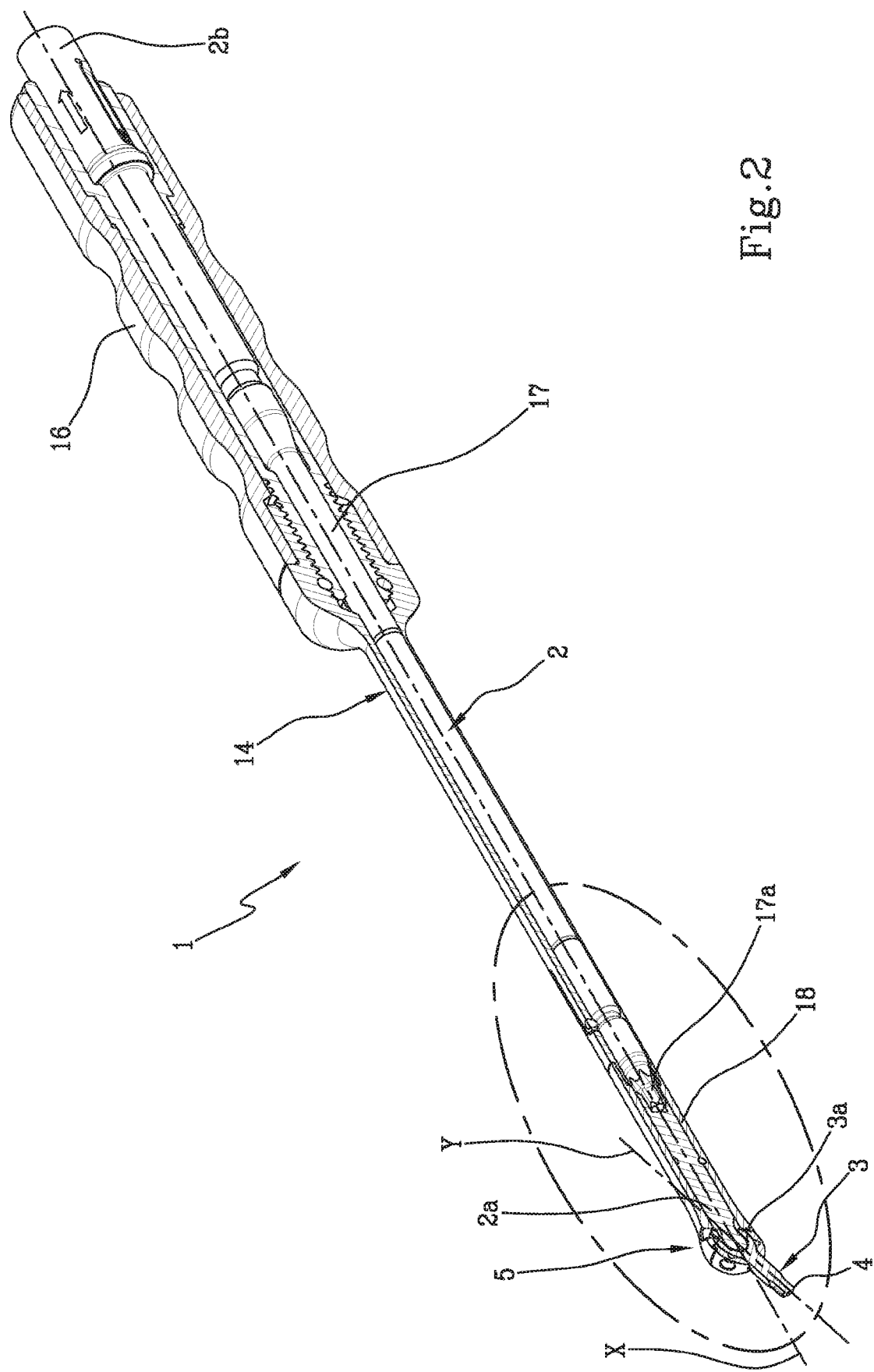
FIG. 2 shows a perspective view in partial longitudinal section of the surgical screwdriver shown in FIG. 1.

In the above figures, the reference number 1 designates, in its entirety, a surgical screwdriver, according to the present invention.

In accordance with a first embodiment shown in FIGS. 1 to 4, the surgical screwdriver 1 is of the fixed tilted-axis type. In this case, in fact, as will be better clarified later in this discussion, the angle of incidence between the screwing operating axis and the motion actuation axis is predetermined and preferably 25°.

In more detail, the surgical screwdriver 1 comprises a first rotating shaft 2 configured to be rotated about a respective longitudinal extension axis "X".

The first shaft 2 can be rotated manually by the surgical operator, or using appropriate electromechanically controlled motorized systems.

The first shaft 2, made in the form of a stem, defines the "input" axis of the rotational motion and, in use, is kept coincident with the incision made in the patient.

The screwdriver 1 also comprises a second rotating shaft 3 extending along a respective development axis "Y" that is transverse to the longitudinal axis "X" of the first shaft 2. The second shaft 3 has a shaped end tip 4 to insert into the screw head (not shown in the attached figures as it is not part of the present invention).

The end tip 4 can have any shape (slotted, cross-shaped, or Allen-shaped, for instance) depending on the seat located on the screw head or other threaded member to be screwed/unscrewed. In the attached figures a Torx-type shaped tip 4, configured, therefore, in the shape of a six-pointed star, is shown for purely illustrative, non-limiting, purposes.

The development axis "Y" of the second shaft 3 therefore defines an "output" axis of the rotational motion and, in use, is arranged coaxially to the longitudinal extension of the screw in order to operate on the screw itself.

Between the first and second shaft 2, 3, there is also a transmission member 5, which is designed to transfer the rotation from the first shaft 2 to the second shaft 3.

The transmission member 5 is preferably interposed between respective first ends 2a, 3a, of the shafts 2, 3, opposite, respectively, the second end 2b of the first shaft 2 and the shaped tip 4 of the second shaft 3.

The transmission member 5 advantageously comprises a homokinetic spherical joint 6, which is therefore able to keep the transmission ratio between the first shaft (input axis) and the second shaft (output axis) constant.

Figure 3:
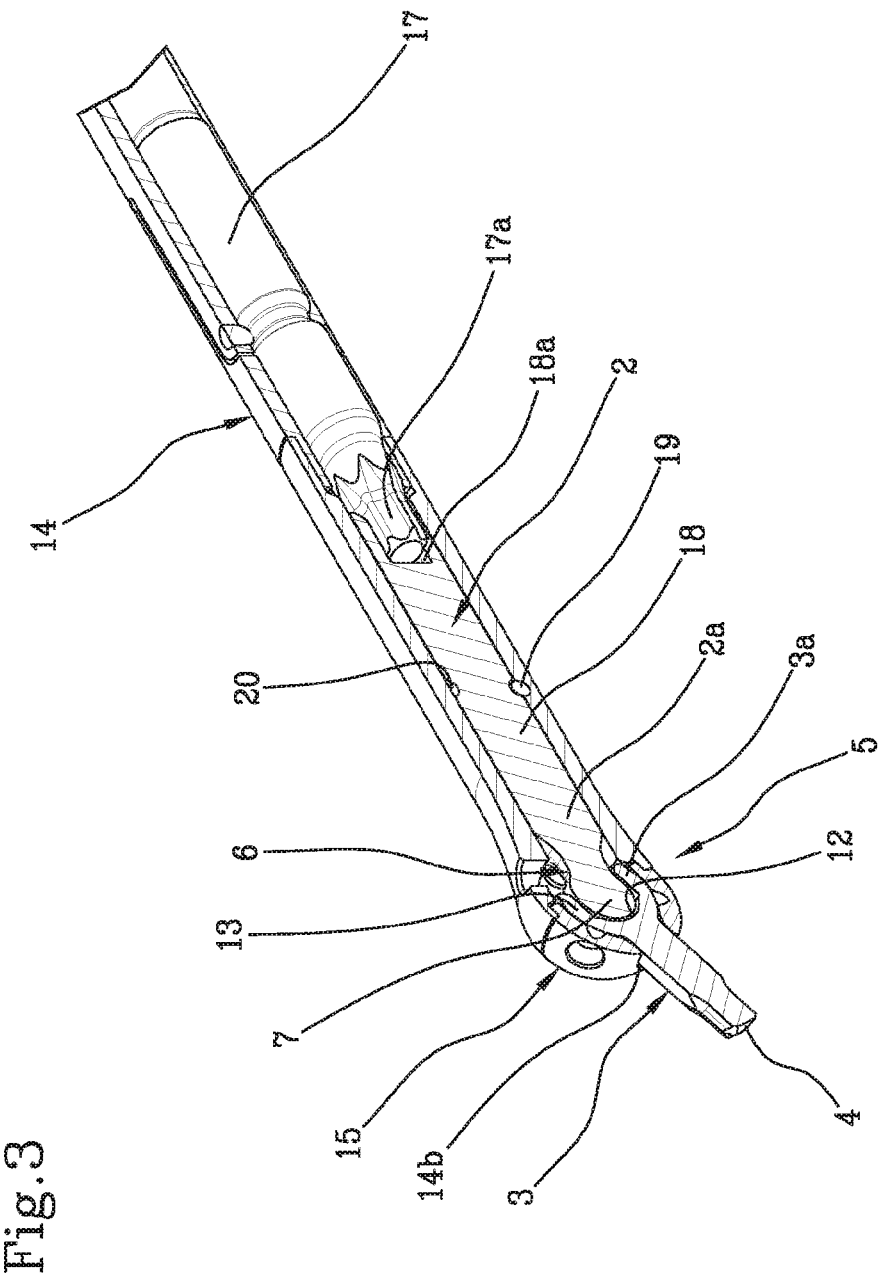
FIG. 3 is an enlarged view of a construction detail of the screwdriver shown in FIG. 2.
Figure 4:
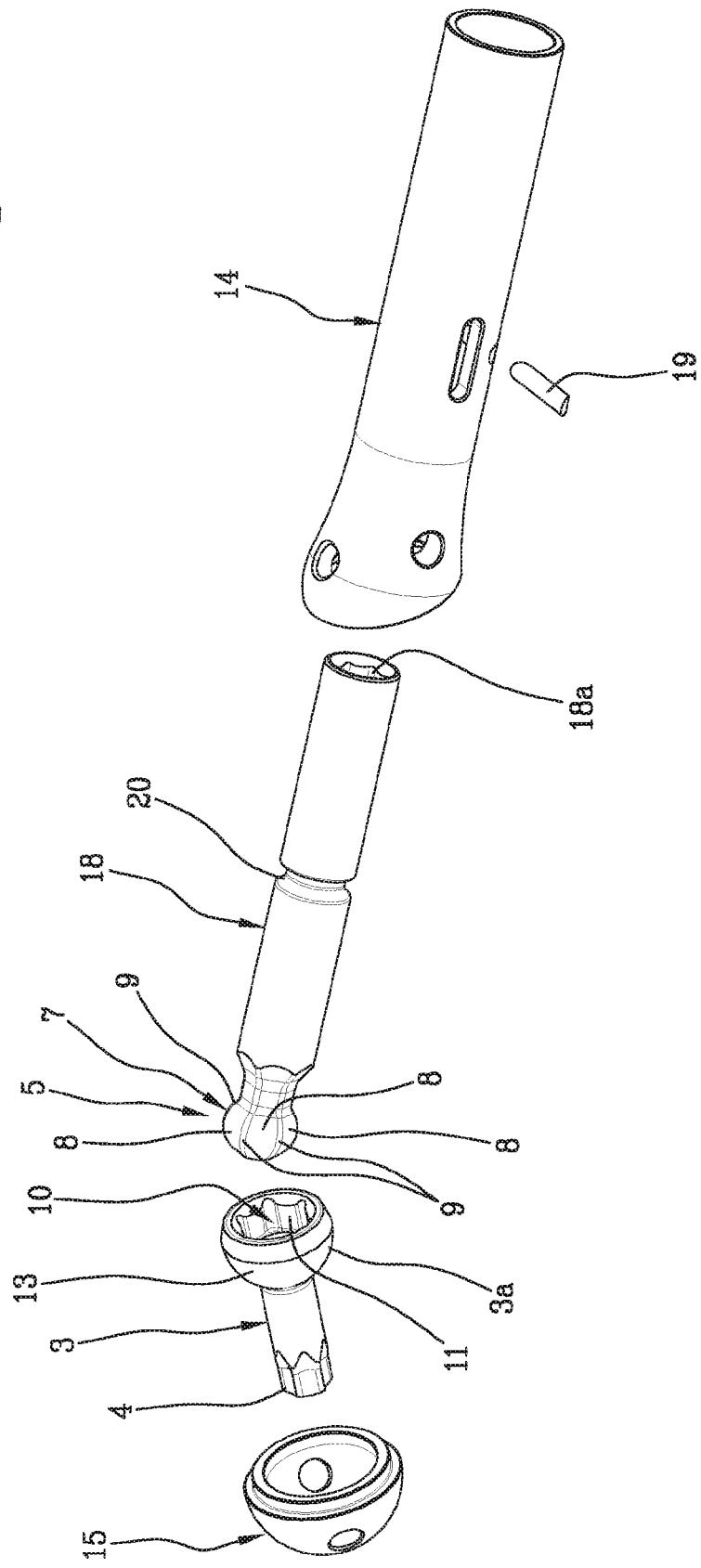
FIG. 4 shows an exploded perspective view of the construction detail highlighted in FIG. 3.

As better shown in FIGS. 3 and 4, the spherical joint 6 comprises a spherical head 7 having at least one lateral facet 8.

A plurality of lateral facets 8 adjacent to each other, each of which defines a respective segment of the spherical head 7, is preferably provided.

Between each pair of adjacent facets 8, there is also an edge 9, which has an arched profile. As a result, the spherical head 7 has a series of arched edges 9 on the outside; these alternate with the facets 8 and extend from two opposite poles of the spherical profile.

The spherical head 7 is joined to the first end 2a, 3a of one of the shafts 2, 3. The head 7 is advantageously made of one piece with the first end 2a of the first shaft 2. In addition, the spherical head 7 has a circular profile along a section plane coinciding with the longitudinal axis "X" (section plane in FIGS. 2 and 3) and a polygonal, preferably hexagonal, profile along a section plane perpendicular to the longitudinal axis "Y".

The homokinetic spherical joint 6 also comprises a cavity 10 counter-shaped to the spherical head 7 and partially surrounding the head 7 itself.

In other words, the cavity 10 is in the shape of a cap and is arranged about a substantially hemispherical portion of the head 7.

The cavity 10 is advantageously located on the first end 3a of the second shaft 3 and preferably made of one piece with the second shaft 3.

Furthermore, the cavity 10 has, inside, a lateral wall 11 defining a polygonal, preferably hexagonal, profile and a hemispherical back wall 12.

In this way, the head 7 and the cavity 10 are bound in rotation (about the axes "X", "Y" of the respective shafts 2, 3) but free to relatively slide to keep the transverse angle of incidence (at 25° in this embodiment) between the two axes "X", "Y".

As is better shown in FIG. 4, the second shaft has a hemispherical enlargement 13 at the first end 3a, which is designed to internally define the above-mentioned cavity 10. From the hemispherical enlargement 13 the second shaft 3, which terminates in the above-mentioned shaped tip 4, extends in the form of a stem.

The screwdriver 1 may also comprise an internally hollow cylindrical sleeve 14, which has a tubular shape and extends along the longitudinal axis "X" of the first shaft 2.

In particular, the sleeve 14 internally accommodates the homokinetic spherical joint 6 and, at least partially, the shafts 2, 3.

In this situation, the second end 2b of the first shaft 2 projects outside a first opening 14a of the sleeve 14. This second end 2b is handled by the operator to actuate the rotation of the first shaft 2 or is engaged in torque limiters or other appropriate transmission and/or motorization systems (not shown as they are not part of the present invention).

In addition, the shaped tip 4 of the second shaft 3 also projects outside a second opening 14b of the sleeve 14 opposite to the first opening 14a and opposite to the second end 2b of the first shaft 2.

In this situation, it should be noted that the openings 14a, 14b of the sleeve are not mutually coaxial, but staggered to define the angle of incidence between the "X, Y" axes.

In fact, the second opening 14b defines the orientation of the development axis "Y" of the second shaft 3, binding this position with respect to the longitudinal axis "X" of the first shaft.

In use, keeping the sleeve 14 fixed, it is possible to rotate the first shaft 2 and therefore also the shaped tip 4, using the transmission member 5 placed inside the sleeve 14 itself.

It should also be noted that the sleeve 14 comprises a projection 15 defining a spherical outer surface for accommodating the homokinetic spherical joint 6. The projection 15 preferably consists of two hemispheres that can be coupled to each other as highlighted in the exploded view in FIG. 4.

The second opening 14b of the sleeve 14 is located on the outer surface of the projection 15. In addition, the projection accommodates the enlargement 13 of the second shaft 3 so that the entire joint 6, during rotation, does not come into contact with the patient's soft tissue surrounding the clamping screw. In other words, only the shaped tip 4 projecting from the sleeve 14 is the only rotating member inside the patient's body. All the rotating members (the shafts and the joint) are advantageously protected inside the sleeve 14. In this situation, it should be noted that the second end 2b of the first shaft 2 remains outside the patient's body.

In addition, an ergonomic portion 16, which is located on the outer surface of the sleeve 14 near the second end 2b of the first shaft 2, is provided to hold the screwdriver 1 in place.

The ergonomic portion 16 enables you to manually hold the sleeve with respect to the incision and with respect to the patient, and, at the same time, to unscrew/screw the screw by operating on the first shaft 2.

Again, in accordance with the first embodiment (FIGS. 1 to 4), the first shaft 2 is preferably made of two portions 17, 18 coaxially joined to each other inside the sleeve 14 and made in the form of respective rods.

In this situation, the second end 2b of the first shaft 2 is located in a first portion 17 distal from the second shaft 3.

The first portion 17 also has a shaped pin 17a, which can be reversibly joined to a respective shaped seat 18a of the second portion 18.

In turn, the second portion 18 has, on the opposite side of the shaped seat 18a, the above-mentioned spherical head 7. The second portion 18 is advantageously held inside the sleeve 14 by means of a connector 19 (FIG. 4) that can be inserted into transverse holes located in the sleeve 14 and through an annular guide 20 located on the second portion 18.

The first portion 17, instead, is held manually inside the sleeve 14 and pushed against the second portion 18 to define the coupling between the pin 17a and the seat 18, which guarantees the transmission of the rotation between the first and second portion 17, 18.

The first portion 17 can advantageously be removed from the sleeve 14 and possibly replaced with other functionally equivalent rods.

Figure 5:
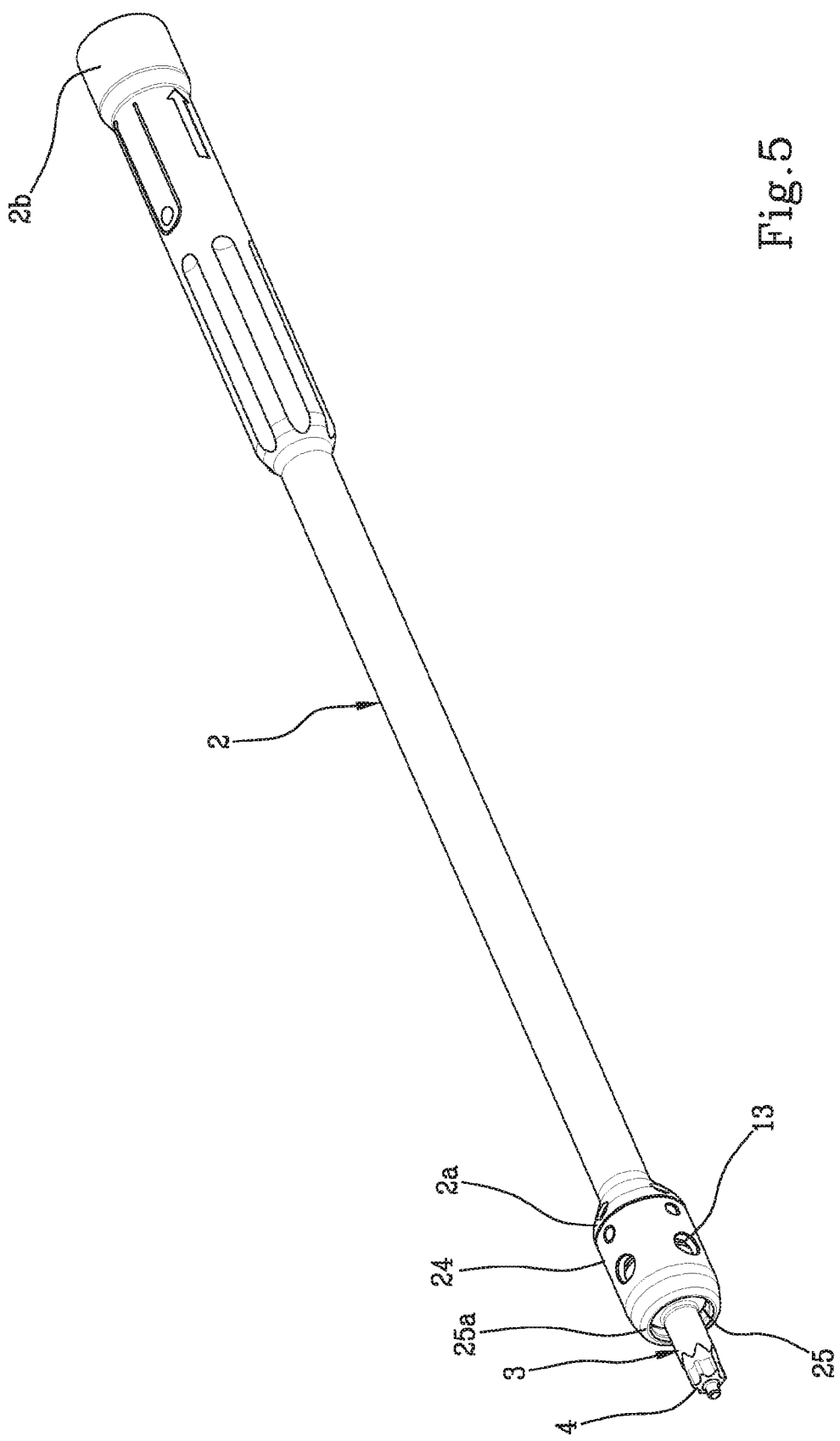
FIG. 5 shows a perspective view of a surgical screwdriver in accordance with a second embodiment of the present invention.
Figure 6:
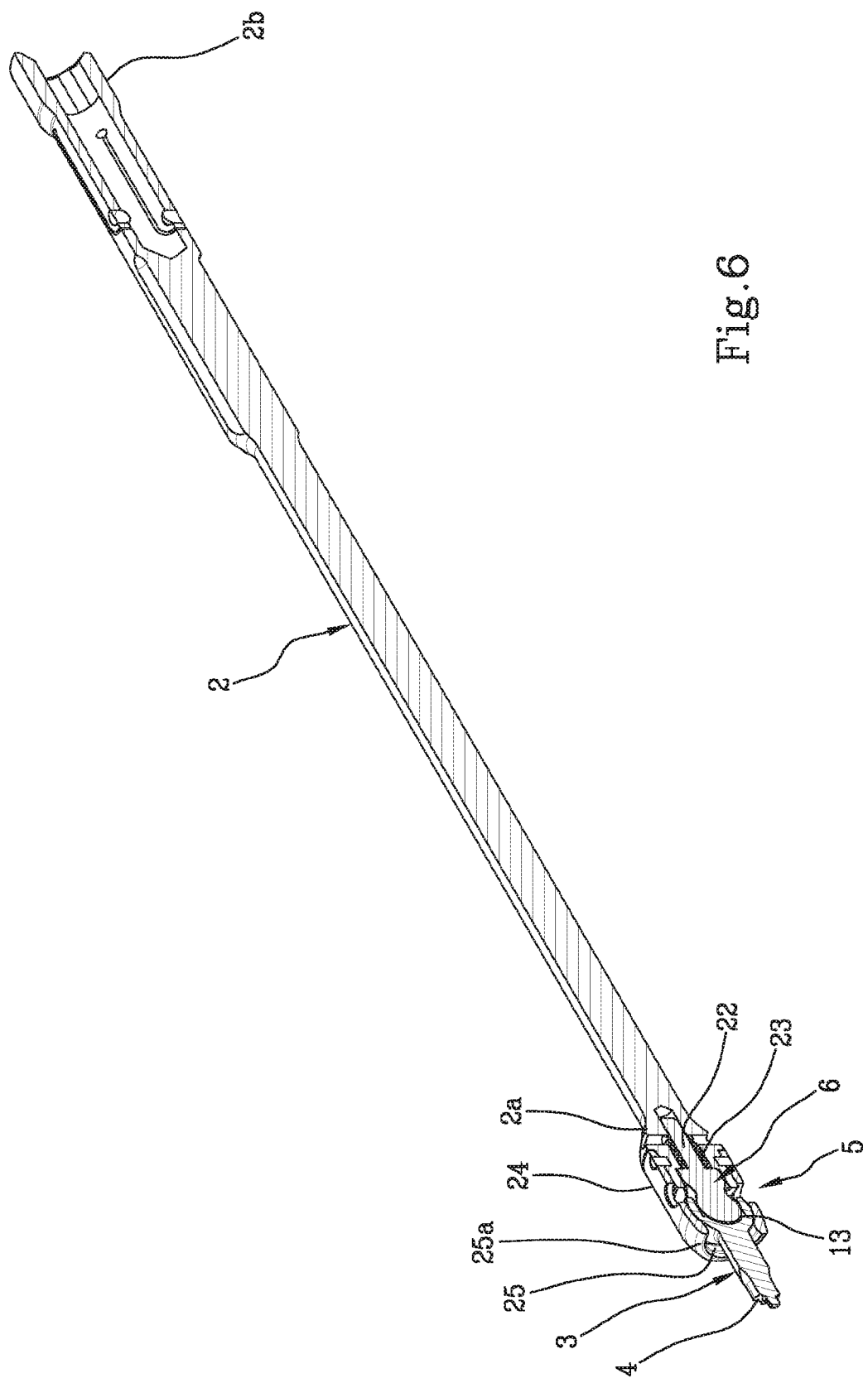
FIG. 6 shows a perspective view in longitudinal section of the surgical screwdriver shown in FIG. 5.
Figure 7:
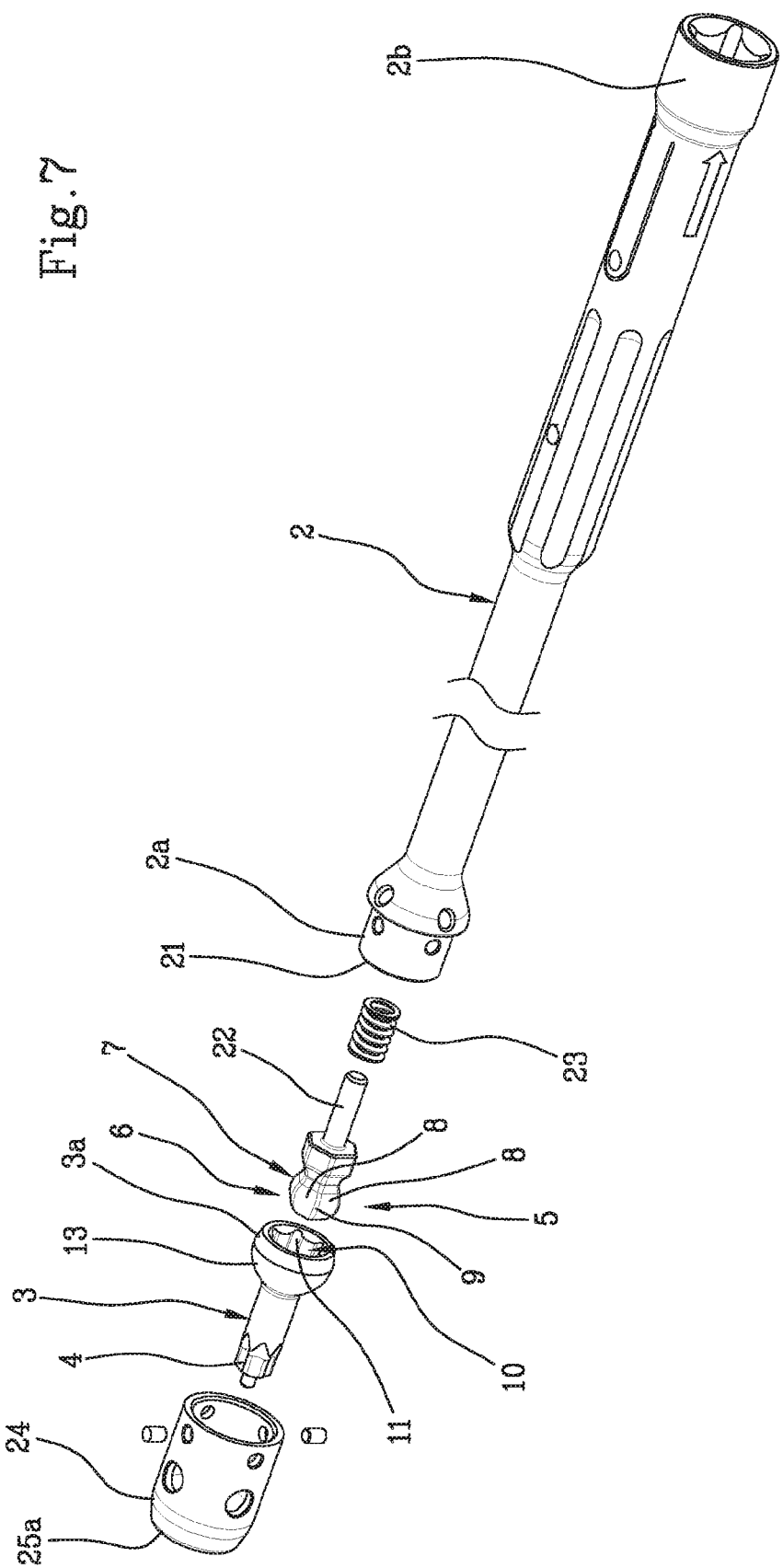
FIG. 7 shows an exploded perspective view of a construction detail of the screwdriver in FIG. 5.

In accordance with a second embodiment shown in FIGS. 5 to 7, a variably tilted-axis screwdriver is provided.

In this situation, the orientation of the shaped tip 4, and the entire second shaft 3, can be changed according to the various needs of their use and within a predetermined range of angles between the two axes "X, Y".

The sleeve 14 can also be used for this embodiment. However, for the sake of clarity, the second embodiment, without the sleeve 14, is shown in the attached figures.

In particular, in this solution the first shaft 2 is made of one piece and the respective first end 2a is equipped with a circular seat 21 coaxial to the longitudinal axis "X".

As better shown in FIGS. 6 and 7, the spherical head 7 is equipped with a coupling pin 22 projecting from the opposite side of the cavity 10 and accommodated inside the circular seat 21.

In addition, an elastic thrust member 23 is provided, interposed between the circular seat 21 and the coupling pin 22, to enable the movement of the spherical head 7 towards the first shaft 2 as better explained later on.

The first end 2a of the first shaft 2 is coaxially engaged to a hollow cylindrical body 24 to internally gather the homokinetic spherical joint 6 (as better shown in FIG. 6).

The cylindrical body 24 has a through opening 25 through which the second shaft 3 and the respective shaped tip 4 partially project. It should be noted that the through opening 25 is much wider than the thickness of the second shaft 3 to allow the second shaft 3 to move inside the opening 25 and to orient the shaped tip 4 by changing the angle of incidence between the axes "X, Y".

In other words, the second shaft 3 is oriented in a plurality of operating configurations, each of which is representative of a respective angle of incidence between the longitudinal axis "X" of the first shaft 2 and the development axis "Y" of the second shaft 3. The tilt of the second shaft 3 can, advantageously, be adjusted according to the position of the screw to be screwed/unscrewed, regardless of the position of the first shaft 2.

Finally, it should be noted that the through opening 25 of the cylindrical body 24 is defined by a perimeter rim 25a that has a width smaller than the diameter of the hemispherical enlargement 13. In this way, the first end 3a of the second shaft 3 always remains contained inside the cylindrical body 24 and, during the handling of the second shaft 3, the spherical surface of the enlargement 13 slides on the rim 25a.

It should be noted that the second shaft 3 is bound in rotation to the first shaft 2 and the head 7 is pushed against the cavity 10 by the elastic member 23. In this way, it is possible to keep the screwdriver 1 compressed against the respective screw, defining a pre-load action of the member 23, in which the shaped tip 4 remains inserted so it is pushed against the seat of the screw head.

In other words, the elastic member 23 keeps the shaped tip 4 pressed against the screw, defining a rotational binding between the second shaft 3 and the screw itself.

The screwdriver 1 described above overcomes the drawbacks of the prior art and entails important advantages.

First of all, the homokinetic spherical joint enables the transmission ratio between the angular velocity of the first shaft 2 and the second shaft 3 to be kept constant.

The rotational movement is, advantageously, more homogeneous, smooth, and, therefore, more precise during the tightening of the screws.

In addition, the angle of incidence can be adjusted according to the position of the screw. In accordance with the second embodiment, it is possible to orient the axis of the second shaft 3 according to the axial position of the screw. The screwdriver 1 is, therefore, very versatile and can be adjusted to the various types of screws and their insertion positions.

A further significant advantage is the very small overall size, especially in the positioning area of the transmission member 5.

This advantage is due to the shape of the spherical joint 6, which enables a considerable reduction in its overall size compared to the known cardan joints.

The surgical operator can, advantageously, make an incision of a very limited size, thus facilitating the minimum invasiveness of the operation.

Finally, another important advantage of the present invention is due to the absence of projecting portions that, when rotating, can interfere with the tissues surrounding the clamping screws.

It should be noted that, in particular, the spherical joint 6 is always contained inside the sleeve 14 or inside the cylindrical body 24. There is, therefore, no risk of direct contact with this moving part and the soft tissue.

In addition, the presence of spherical surfaces and, therefore, the absence of outer edges, eliminates any possible damage to the soft tissues resulting from unintentional contact between the screwdriver 1 and the tissues themselves.

The invention claimed is:

1. A surgical screwdriver comprising:
   a first rotating shaft configured to be rotated about a respective longitudinal axis;
   a second rotating shaft extending along a respective development axis and having a shaped end tip which can be inserted into the head of a screw;
   a transmission member having a homokinetic spherical joint interposed between respective first ends of the shafts to transfer the rotation from the first rotating shaft to the second rotating shaft;
   a cylindrical sleeve which is internally hollow to accommodate at least partially said shafts and said homokinetic spherical joint,
   wherein said first rotating shaft has a second end opposite to the first end and projecting out of a first opening of the sleeve,
   wherein said shaped end tip of the second rotating shaft projects out of a second opening of the sleeve opposite to the first opening of the sleeve, and
   wherein said first rotating shaft comprises two discrete portions coaxially and detachably joined to each other inside the sleeve, said second end of the first rotating shaft being located in one of said portions which is distal from the second rotating shaft;
   wherein said openings of the sleeve are not coaxial with each other, and said second opening defines the development axis of the second rotating shaft transverse to the longitudinal axis of the first rotating shaft.

2. The screwdriver according to claim 1, wherein said homokinetic spherical joint comprises a spherical head having at least one lateral facet and a cavity counter-shaped to said head and partially surrounding the head itself.

3. The screwdriver according to claim 2, wherein said spherical head comprises a plurality of lateral facets adjacent to one another and each of which defining a respective segment of the spherical head; said head further comprising a plurality of edges each of which is interposed between two adjacent facets.

4. The screwdriver according to claim 2, wherein said spherical head is joined to the first end of one of said shafts and the spherical head comprises a circular profile along a section plane coinciding with the axis of the respective shaft, and a polygonal profile along a section plane perpendicular to the axis of the respective shaft.

5. The screwdriver according to claim 2, wherein said spherical head is joined to the first end of the first rotating shaft and said cavity is located on the first end of the second rotating shaft, said first end of the second rotating shaft being arranged on the opposite side with respect to said shaped end tip.

6. The screwdriver according to claim 1, wherein said sleeve comprises a projection defining a spherical outer surface for accommodating said spherical joint, and said second opening of the sleeve is located on the outer surface of the projection.

7. The screwdriver according to claim 1, wherein said sleeve comprises an ergonomic portion arranged on an outer surface of the sleeve which is close to the second end of the first shaft, said shafts being rotatable inside the sleeve about the respective axes and with respect to the sleeve itself.

* * * * *